(12) United States Patent
Hsu et al.

(10) Patent No.: US 8,420,119 B2
(45) Date of Patent: Apr. 16, 2013

(54) DRUG COMPOSITION FOR TREATING TUMOR WITH POLYMERIC MICELLE ENCAPSULATING ANTI-NEOPLASTIC

(75) Inventors: Yuan-Hung Hsu, Taoyuan County (TW); Chu-Chun Hsueh, Taipei (TW); Yuan-Chia Chang, Taipei (TW); Jui-Mei Lu, Hsinchu County (TW); Pei Kan, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/265,802

(22) PCT Filed: Aug. 20, 2009

(86) PCT No.: PCT/CN2009/073382
§ 371 (c)(1),
(2), (4) Date: Dec. 30, 2011

(87) PCT Pub. No.: WO2010/121455
PCT Pub. Date: Oct. 28, 2010

(65) Prior Publication Data
US 2012/0100220 A1  Apr. 26, 2012

(30) Foreign Application Priority Data
Apr. 21, 2009  (CN) .......................... 2009 1 0132138

(51) Int. Cl.
*A61K 9/14* (2006.01)
*A61K 9/51* (2006.01)
*A61K 31/44* (2006.01)
*A01N 43/42* (2006.01)

(52) U.S. Cl.
USPC ........... 424/450; 424/489; 424/451; 514/283; 977/773

(58) Field of Classification Search ................... None
See application file for complete search history.

(56) References Cited

U.S. PATENT DOCUMENTS

| | | | |
|---|---|---|---|
| 2002/0156047 A1* | 10/2002 | Zhao ................................ | 514/58 |
| 2003/0059465 A1* | 3/2003 | Unger et al. .................. | 424/465 |
| 2004/0234494 A1 | 11/2004 | Seo et al. | |
| 2007/0104654 A1* | 5/2007 | Hsieh et al. ..................... | 424/46 |
| 2007/0258889 A1* | 11/2007 | Douglas et al. .............. | 424/1.37 |
| 2008/0166382 A1 | 7/2008 | Hsieh et al. | |
| 2008/0274173 A1* | 11/2008 | Sill et al. ....................... | 424/450 |

FOREIGN PATENT DOCUMENTS

| | | |
|---|---|---|
| CN | 1531566 A | 9/2004 |
| CN | 100998870 A | 7/2007 |
| WO | WO 03/074026 A1 | 9/2003 |

OTHER PUBLICATIONS

International Search Report for PCT/CN2009/073382 dated Feb. 4, 2010.

* cited by examiner

*Primary Examiner* — Frederick Krass
*Assistant Examiner* — Isaac Shomer
(74) *Attorney, Agent, or Firm* — Birch, Stewart, Kolasch & Birch, LLP

(57) ABSTRACT

This present disclosure relates to pharmaceutical compositions for treating tumors using a polymeric micelle encapsulating an anti-tumor drug. The polymeric micelle comprises block copolymers comprising at least one hydrophilic block, at least one hydrophobic block, and at least one zwitterion. The present disclosure also relates to methods of enhancing the solubility of such drugs, methods of increasing the blood circulating time of such drugs, and methods of delivering such drugs to one or more solid tumors.

9 Claims, 8 Drawing Sheets

| | 0 | | 0.5 | | 1 | | 1.5 | | 2 | | 4 | | 8 | |
|---|---|---|---|---|---|---|---|---|---|---|---|---|---|---|
| | % | S.D. | % | S.D. | % | S.D. | % | S.D. | % | S.D. | % | S.D. | % | S.D. |
| CPT-DMSO | 0 | 0 | -- | -- | 48.2 | 0.33 | -- | -- | 73.89 | 0.6 | 87.21 | 0.94 | 94.18 | 0.15 |
| CC201 | 0 | 0 | -- | -- | 3.2 | 0.11 | -- | -- | 5.8 | 0.26 | 10.1 | 0.25 | 17.5 | 0.89 |
| CC301 | 0 | 0 | -- | -- | 2.1 | 0 | -- | -- | -- | -- | 6.2 | 0 | 10.8 | 0.1 |
| CC701 | 0 | 0 | -- | -- | 6.8 | 0.07 | -- | -- | -- | -- | 18.2 | 0.39 | 28.3 | 0.35 |
| CV201 | 0 | 0 | -- | -- | 1.8 | 0.13 | 2.3 | 0.31 | 2.6 | 0.21 | 4.1 | 0.21 | 5.5 | 0.2 |
| CCP201 | 0 | 0 | -- | -- | 1 | 0.08 | -- | -- | 2.7 | 0.09 | 4.5 | 0.15 | 7 | 0.13 |
| SCP201 | 0 | 0 | 0.21 | | 0.39 | | | | 0.61 | | 1.48 | | 2.65 | |

| | 0 | | 0.5 | | 1 | | 2 | | 4 | | 8 | |
|---|---|---|---|---|---|---|---|---|---|---|---|---|
| | % | S.D. | % | S.D. | % | S.D. | % | S.D. | % | S.D. | % | S.D. |
| CPT-DMSO | 100 | 0 | -- | -- | -- | -- | 26.4 | 2.41 | 18.1 | 0.77 | 17.9 | 0.75 |
| CC201 | 100 | 0 | -- | -- | -- | -- | 77.3 | 2.8 | 74.6 | 2.9 | 72.2 | 2.1 |
| CC301 | 100 | 2.2 | -- | -- | -- | -- | 67.3 | 1.4 | 63 | 0.8 | 55.4 | 0.7 |
| CC701 | 100 | 0 | -- | -- | -- | -- | 59.3 | 1.03 | 58.1 | 1.35 | 56.2 | 2.11 |
| CV201 | 100 | 0 | -- | -- | 86 | 0.64 | -- | -- | 78 | -- | 75 | 1.77 |
| CCP201 | 100 | 0 | -- | -- | 82.4 | 4.5 | 77.5 | 1.1 | 74.3 | 0.9 | 73 | 4.9 |
| SCP201 | 100 | | 93 | | 91.8 | | 91.1 | | 91.1 | | 89.7 | |

| | 0.25 | | 0.5 | | 1 | | 2 | | 4 | | 7 | | 24 | |
|---|---|---|---|---|---|---|---|---|---|---|---|---|---|---|
| | ng/ml | S.D. | ng/ml | S.D. | ng/ml | S.D. | ng/ml | S.D. | ng/ml | S.D. | ng/ml | S.D. | ng/ml | S.D. |
| CPT-DMSO | 19.4 | 5.8 | 11.6 | 4.7 | 3.1 | 2.6 | 0.3 | 0.5 | N.D | N.D | N.D | N.D | N.D | N.D |
| CC201 | 33.3 | 19.1 | 25.6 | 11.4 | 15.8 | 12.9 | 12.9 | 5.6 | 4.9 | 3.9 | 0.8 | 0.8 | N.D | N.D |
| CCP201 | 22.3 | 12.6 | 13.8 | 5.0 | 9.3 | 7.5 | 6.9 | 4.7 | 3.6 | 1.1 | 2.0 | 1.5 | 1.2 | 1.4 |
| CV201 | 80.0 | 5.7 | 43.0 | 4.2 | 9.0 | 0.3 | 0.5 | 0 | N.D | N.D | N.D | N.D | N.D | N.D |

| | 0.033 | | 0.083 | | 0.1 | | 0.2 | | 0.250 | | 0.3 | | 0.500 | | 1.0 | |
|---|---|---|---|---|---|---|---|---|---|---|---|---|---|---|---|---|
| | ng/ml | S.D. | ng/ml | S.D. | ng/ml | S.D. | ng/ml | S.D. | ng/ml | S.D. | ng/ml | S.D. | ng/ml | S.D. | ng/ml | S.D. |
| SC201 | 4137.6 | 868.9 | 2265.2 | 158.6 | -- | -- | -- | -- | 320.8 | 35.3 | -- | -- | 213.2 | 27.8 | 164.2 | 49.3 |
| SCP201 | 26066.6 | 2737.0 | 505.3 | 109.2 | -- | -- | -- | -- | 2053.0 | 277.2 | -- | -- | 1503.2 | 75.2 | 1127.2 | 126.2 |
| SN38-DMSO | -- | -- | -- | -- | 710.8 | 61.7 | 505.3 | 109.2 | -- | -- | 265.3 | 5.6 | 143.4 | 27.3 | 32.3 | 3.6 |

| | 1.5 | | 2.0 | | 4.0 | | 6.0 | | 8.0 | | 9.0 | | 24.0 | | 27.0 | |
|---|---|---|---|---|---|---|---|---|---|---|---|---|---|---|---|---|
| | ng/ml | S.D. | ng/ml | S.D. | ng/ml | S.D. | ng/ml | S.D. | ng/ml | S.D. | ng/ml | S.D. | ng/ml | S.D. | ng/ml | S.D. |
| SC201 | 144.0 | 17.3 | 95.5 | 39.2 | 55.6 | 0.6 | 41.8 | 3.8 | -- | -- | 30.9 | 8.3 | 26.8 | 8.3 | 25.7 | 0.3 |
| SCP201 | 936.1 | 56.2 | 826.1 | 74.4 | 631.0 | 66.3 | 398.1 | 83.6 | -- | -- | 194.7 | 9.8 | 160.5 | 17.7 | 141.3 | 11.3 |
| SN38-DMSO | -- | -- | 12.5 | 0.6 | 9.0 | 0.6 | -- | -- | 7.3 | 0.7 | -- | -- | 1.0 | 0.30 | -- | -- |

|  | 0 | | 4 | | 8 | | 11 | | 13 | |
|---|---|---|---|---|---|---|---|---|---|---|
|  | Vol. | S.D. | Vol. | S.D. | Vol. | S.D. | Vol. | S.D. | Vol. | S.D. |
| CONTROL | 561.4 | 132.8 | 548.9 | 83.5 | 730.3 | 144.8 | 927.0 | 235.7 | 914.1 | 301.6 |
| CPT11 (10 mg/kg) | 469.6 | 136.6 | 745.8 | 119.5 | 723.4 | 199.3 | 740.8 | 154.5 | 786.0 | 251.4 |
| CCP201 (9 mg/kg) | 337.0 | 84.1 | 469.9 | 91.2 | 556.5 | 100.7 | 575.8 | 79.9 | 614.3 | 88.6 |
| CCP201 (18 mg/kg) | 557.5 | 204.7 | 492.2 | 141.9 | 487.1 | 224.5 | 479.3 | 167.6 | 427.8 | 131.9 |
|  | 15 | | 18 | | 20 | | 22 | | 27 | |
|  | Vol. | S.D. | Vol. | S.D. | Vol. | S.D. | Vol. | S.D. | Vol. | S.D. |
| CONTROL | 1024.4 | 190.4 | 1259.8 | 267.2 | 1391.6 | 275.5 | 1284.0 | 227.6 | 1958.5 | 236.8 |
| CPT11 (10 mg/kg) | 757.5 | 280.9 | 879.8 | 275.0 | 902.7 | 179.2 | 927.3 | 270.8 | 1217.6 | 209.4 |
| CCP201 (9 mg/kg) | 621.1 | 62.3 | 675.0 | 118.8 | 565.2 | 334.8 | 554.7 | 290.4 | 924.0 | 370.2 |
| CCP201 (18 mg/kg) | 468.7 | 140.8 | 427.8 | 131.9 | 473.3 | 132.8 | 436.7 | 68.2 | 685.2 | 245.7 |

|  | 0 |  | 1 |  | 3 |  | 6 |  | 8 |  |
|---|---|---|---|---|---|---|---|---|---|---|
|  | Vol. | S.D. | Vol. | S.D. | Vol. | S.D. | Vol. | S.D. | Vol. | S.D. |
| CONTROL | 150.6 | 47.1 | 147.5 | 22.5 | 191.5 | 35.5 | 292.7 | 46.5 | 351.9 | 48.6 |
| CPT11 (10 mg/kg) | 142.0 | 30.1 | 175.1 | 34.4 | 192.0 | 35.6 | 215.0 | 47.5 | 251.2 | 47.0 |
| CPT11 (40 mg/kg) | 152.1 | 27.6 | 184.6 | 32.1 | 239.3 | 48.5 | 215.0 | 51.9 | 184.7 | 56.1 |
| SCP201 (4 mg/kg) | 156.1 | 33.9 | 192.6 | 34.8 | 215.5 | 31.6 | 276.9 | 50.3 | 313.8 | 60.5 |
| SCP201 (10mg/kg) | 134.1 | 23.6 | 142.9 | 23.6 | 181.6 | 27.7 | 176.1 | 23.9 | 151.0 | 23.4 |
| SCP201 (20 mg/kg) | 156.7 | 33.7 | 157.8 | 30.2 | 214.4 | 42.9 | 141.1 | 29.3 | 97.1 | 21.8 |
|  | 10 |  | 13 |  | 15 |  | 17 |  | 20 |  |
|  | Vol. | S.D. | Vol. | S.D. | Vol. | S.D. | Vol. | S.D. | Vol. | S.D. |

Figure 7 (Cont)

| | | | | | | | | | | | |
|---|---|---|---|---|---|---|---|---|---|---|---|
| CONTROL | 421.6 | 60.4 | 518.3 | 71.2 | 587.1 | 87.7 | 648.4 | 100.0 | 771.8 | 128.3 |
| CPT11 (10 mg/kg) | 262.1 | 61.1 | 263.5 | 53.1 | 274.1 | 53.8 | 293.7 | 58.9 | 301.4 | 55.2 |
| CPT11 (40 mg/kg) | 161.7 | 44.5 | 110.2 | 28.1 | 70.9 | 17.6 | 59.1 | 15.9 | 37.8 | 8.4 |
| SCP201 (4 mg/kg) | 345.3 | 77.3 | 363.6 | 79.2 | 379.9 | 96.0 | 402.3 | 99.7 | 404.6 | 99.0 |
| SCP201 (10mg/kg) | 141.8 | 22.5 | 110.7 | 21.4 | 101.1 | 22.0 | 101.0 | 24.5 | 104.8 | 25.0 |
| SCP201 (20 mg/kg) | 72.9 | 15.3 | 40.7 | 8.1 | 27.1 | 5.5 | 22.4 | 4.4 | 14.4 | 4.8 |

DRUG COMPOSITION FOR TREATING TUMOR WITH POLYMERIC MICELLE ENCAPSULATING ANTI-NEOPLASTIC

The present disclosure relates to pharmaceutical compositions for treating tumors using a polymeric micelle encapsulating an anti-tumor drug. In one embodiment, the polymeric micelle comprises block copolymers comprising at least one hydrophilic block, at least one hydrophobic block, and at least one zwitterion. And the anti-tumor drug is, for example, hydrophobic. The present disclosure also relates to methods of enhancing the solubility of anti-tumor drugs, methods of increasing the blood circulating time of anti-tumor drugs, and methods of delivering anti-tumor drugs to one or more solid tumors.

Many anti-tumor drugs are hydrophobic and therefore would have limited solubility in an aqueous medium. For example, camptothecin (CPT), an inhibitor of DNA Topoisomerase I, has been proven to be a possible therapeutic candidate for treating tumors. CPT has a terminal ring converting between a lactone form in an acidic medium (pH<5) and a ring-opened carboxylate form in an alkaline medium (pH>8), but only the lactone form CPT is pharmaceutically active. This active form, however, is hydrophobic and therefore presents difficulties in delivery in a physiological environment.

There exists another problem in delivering CPT or its analogues. For instance, because the lactone form CPT and the carboxylate form CPT are inter-convertible in a pH-dependant equilibrium, the lactone form CPT could rapidly convert to the carboxylate form CPT in a physiological environment. Furthermore, because the carboxylate form CPT can bind with human serum albumin (HSA) very efficiently, more lactone form CPT would be converted into the carboxylate form CPT at the presence of HAS for reaching an equilibrium.

Like CPT, its biological analogues, such as 7-ethyl-10-hydroxycamptothecin (SN38, the metabolic product of 7-ethyl-10-[4-(1-piperidino)-1-piperidono]carbonyloxy camptothecin (CPT11)), and some other anti-tumor drugs also have poor solubility and similar active-inactive form conversion problems in a physiological environment. Because these drugs might also be highly toxic and rapidly metabolized, it is desirable to introduce and deliver desirable therapeutic levels of such drugs into solid tumors and in the meantime reduce their toxicity.

Several methods have been developed for these purposes, including using micelles as carriers, since a well-designed micelle, such as a biodegradable and biocompatible micelle, is capable of solubilizing hydrophobic anti-tumor drugs in a physiological environment, increasing the blood circulating time of such drugs, and thus delivering desirable therapeutic levels of such drugs to solid tumors. Nonetheless, better alternatives are still needed.

The present inventors have surprisingly found that certain polymeric micelle could provide better properties in delivering an anti-tumor drug. In one embodiment, the present disclosure provides pharmaceutical compositions for treating tumors using a polymeric micelle encapsulating an anti-tumor drug, wherein the polymeric micelle comprises block copolymers comprising one or more hydrophilic blocks, one or more hydrophobic blocks, and one or more zwitterions.

The hydrophobic block may comprise at least one entity chosen, for example, from polycaprolactone (PCL), polyvalerolactone (PVL), poly(lactide-co-glycolide) (PLGA), polylactic acid (PLA), polybutyrolactone (PBL), polyglycolide, and polypropiolactone (PPL). The hydrophilic block may comprise at least one entity chosen, for example, from polyethylene glycol (PEG), hyaluronic acid (HA), and poly-γ-glutamine acid (γ-PGA). And the zwitterion may comprise at least one entity chosen, for example, from phosphorylcholine (PC), sulfobetaine (NS), and amino acids. The anti-tumor drugs encapsulated within the polymeric micelle might be a single drug or a combination of different drugs.

The present disclosure also relates to methods of enhancing the solubility of anti-tumor drugs, methods of increasing the blood circulating time of such drugs, and methods of delivering such drugs to one or more solid tumors. These methods use above-mentioned polymeric micelle to encapsulate at lease one anti-tumor drug, to increase the solubility, blood circulating time of such drugs, and/or to deliver such drugs to one or more solid tumors.

It is to be understood that both the foregoing general description and the following detailed description are exemplary and explanatory only and are not restrictive of the invention as claimed.

The accompanying drawings, which are incorporated in and constitute a part of this specification, illustrate several embodiments of the invention and together with the description, serve to explain the principles of the invention.

Figure 1:
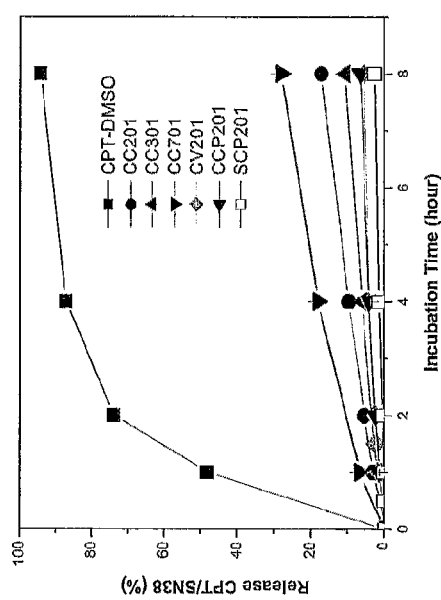
FIG. 1 illustrates the release profile of CPT (or SN38) over incubation time for various compositions using dialysis bag.

Reference is now be made in detail to the exemplary embodiments of the invention, examples of which are illustrated in the accompanying drawings.

The present disclosure relates to a pharmaceutical composition for treating tumor using a polymeric micelle encapsulating an anti-tumor drug. The polymeric micelle comprises block copolymers comprising at least one hydrophilic block, at least one hydrophobic block, and at least one zwitterion. The block copolymer may, for example, be amphiphilic. In one embodiment, the hydrophobic block has a molecular weight ranging, for example, from about 500 to about 30,000 Daltons. The hydrophobic block may comprise, for example, at least one entity chosen, for example, from polycaprolactone (PCL), polyvalerolactone (PVL), poly(lactide-co-glycolide) (PLGA), polylactic acid (PLA), polybutyrolactone (PBL), polyglycolide, and polypropiolactone (PPL). The hydrophilic block has a molecular weight ranging, for example, from about 500 to about 30,000 Daltons. The hydrophilic block may comprise, for example, at least one entity chosen from polyethylene glycol (PEG), hyaluronic acid (HA), and poly-γ-glutamine acid (γ-PGA). And the zwitterion may comprise, for example, at least one entity chosen from phosphorylcholine (PC), sulfobetaine (NS), and amino acids.

An exemplary block copolymer, PEG-PCL-PC, has the following structure:

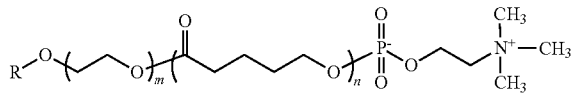

wherein R is a hydrogen atom, a $C_{1-6}$alkyl group, a benzyl group, or an acyl group, which might be either unsubstituted or substituted by a functional group, which may be protected; m and n, which may be the same or different, are each an integer. Preferably, m and n are individually an integer of 10-100. More preferably, m is an integer of 30-85 and n is an integer of 10-80. The block copolymers disclosed herein can be produced by the methods disclosed in the United States Patent Application Publication No. 2007/0104654.

Above the critical micelle concentration (CMC), the block copolymers disclosed herein are able to form a polymeric micelle in an aqueous medium, in which the hydrophobic parts are buried in the core. The polymeric micelle may, for example, have a diameter of about 20-1,000 nm. It may be essentially non-immunogenic because of the chain flexibility of the hydrophilic block and the existence of the zwitterion. The hydrophobic block is able to be decomposed by enzyme or hydrolysis. The polymeric micelle is biodegradable and/or biocompatible. Therefore, after the hydrophobic block is decomposed, the remaining harmless substances such as the hydrophilic block and the zwitterion can be dissolved in blood and then removed from renal system.

The anti-tumor drugs encapsulated in the polymeric micelle may be a single drug or a combination of different drugs.

The polymeric micelle disclosed herein can serve as an effective drug carrier, and is able to take up at least one hydrophobic drug into its hydrophobic core to form a pharmaceutical composition. Accordingly, the present disclosure also relates to methods of enhancing the solubility of anti-tumor drugs, methods of increasing the blood circulating time of such drugs, and methods of delivering such drugs to one or more solid tumors. These methods use the polymeric micelle disclosed herein to encapsulate at least one anti-tumor drug, to increase the solubility, effective or potency of the drug, and to deliver the drug to one or more solid tumors. In one embodiment, the present disclosure relates to a method of delivering an anti-tumor drug to a solid tumor, comprising encapsulating the anti-tumor drug in the polymeric micelle disclosed herein to form an encapsulation complex, and delivering the encapsulation complex to human body by a known means of drug delivery, such as via oral administration, transdermal administration, injection, or inhalation.

The polymeric micelle encapsulating at least one anti-tumor drug disclosed herein can be prepared, for example, by the following processes. Certain amounts of anti-tumor drugs and block copolymers are stirred and dissolved in 1 ml dimethyl sulfoxide (DMSO). After DMSO is removed by freeze-drying, 1 ml of 10% of sucrose is added, and the freeze-dried solid is then dissolved to form a suspension. After subject to ultra-sonication for ten minutes, the suspension is further filtered by a 0.45 μm filter to remove un-encapsulated drug crystals and the polymeric micelle encapsulating at least one anti-tumor drug could be formed. The drug encapsulation efficiency (E.E.) was calculated using the following formula:

$$E.E(\%) = \frac{\text{total mass of drug in micelle}}{\text{total mass of drug as in loading}} \times 100$$

Table 1 shows the selection of various anti-tumor drugs (CPT or SN38), block copolymers, and their amounts used in each preparation. PEG, PCL, PVL, and PC represent polyethylene glycol, polycaprolactone, polyvalerolactone, and phosphorylcholine, respectively, and the numbers attached represent approximate molecular weights of PEG, PCL, and PVL. For example, $PEG_{5000}PCL_{1900}PC$ represents a block copolymer comprising a PEG with molecular weight of about 5000 Daltons, which is linked to a PCL with molecular weight of about 1900 Daltons, which is further linked to a PC.

The Composition Code is given arbitrarily to represent different compositions. CC201, CC301, CC701, CV201, and SC201 compositions do not comprise any zwitterion, and are thus for control purposes.

The particle size distributions can be obtained by, for example, a laser particle size analyzer (Coulter N4 plus), and the quantities of encapsulated CPT or SN38 in each preparation can be determined by HPLC. P.S., P.I. and E.E. in Table 1 denote particle size, polydispersity index, and encapsulation efficiency, respectively. These parameters can be measured and/or calculated according to the techniques known in the art.

TABLE 1

| Composition Code | Block copolymer (10 mg) | CPT (mg) | SN38 (mg) | P.S. (nm) | P.I. | E.E. (%) |
|---|---|---|---|---|---|---|
| CC201 | $PEG_{5000}PCL_{1900}$ | 1 | | 141.1 ± 58.4 | ≦0.326 | ≧86% |
| CC301 | $PEG_{5000}PCL_{3700}$ | 1 | | 128.6 ± 49.8 | ≦0.320 | ≧95% |
| CC701 | $PEG_{2000}PCL_{2000}$ | 1 | | 127.8 ± 53.7 | ≦0.310 | ≧93% |
| CV201 | $PEG_{5000}PVL_{3600}$ | 1 | | 147.7 ± 54.7 | ≦0.266 | ≧85% |
| CCP201 | $PEG_{5000}PCL_{1900}PC$ | 1 | | 144.3 ± 46.5 | ≦0.329 | ≧82% |
| CCP601 | $PEG_{5000}PCL_{8400}PC$ | 1 | | 110.6 ± 39.7 | ≦0.329 | ≧86% |
| SC201 | $PEG_{5000}PCL_{1900}$ | | 1 | 157.4 ± 38.1 | ≦0.260 | ≧80% |
| SCP201 | $PEG_{5000}PCL_{1900}PC$ | | 1 | 151.5 ± 45.9 | ≦0.264 | ≧85% |
| SCP202 | $PEG_{5000}PCL_{1900}PC$ | | 2 | 125.3 ± 45.9 | ≦0.247 | ≧96% |
| SCP203 | $PEG_{5000}PCL_{1900}PC$ | | 3 | 112.7 ± 45.9 | ≦0.305 | ≧94% |

This invention is explained in more detail based on the following Examples, which should not be construed as limiting the scope of this invention.

EXAMPLE 1

Release Test Using Dialysis Bag

A 50 μL solution of a pharmaceutical composition, which was prepared according to the method as set forth above, was added into a dialysis bag having a molecular weight cutoff of about 3,500 Daltons, and then was dialyzed against a 50 ml phosphate buffered saline (PBS) (pH 7.4) at 37° C. After 1, 2, 4, and 8 hours of dialysis, 250 μL out-of-bag buffers were taken respectively, and then each was then mixed with 750 μL methanol (in 0.6N HCl). The quantity of each drug, which was released from the polymeric micelle and then dialyzed into the out-of-bag buffer, was determined by HPLC. A 50 μL CPT containing DMSO solution (CPT-DMSO) was used as a control.

FIG. 1 illustrates the release profile of CPT (or SN38) over incubation time for various compositions using dialysis bag and Table 2 shows the original data.

TABLE 2

| | \%[a] | S.D.[b] | \% | S.D. | \% | S.D. | \% | S.D. | \% | S.D. | \% | S.D. |
|---|---|---|---|---|---|---|---|---|---|---|---|---|
| | \multicolumn{12}{c}{Hour(s)} |
| | \multicolumn{2}{c}{0.5} | \multicolumn{2}{c}{1} | \multicolumn{2}{c}{1.5} | \multicolumn{2}{c}{2} | \multicolumn{2}{c}{4} | \multicolumn{2}{c}{8} |
| CPT-DMSO | — | — | 48.2 | 0.3 | — | — | 73.9 | 0.6 | 87.2 | 0.9 | 94.2 | 0.2 |
| CC201 | — | — | 3.2 | 0.1 | — | — | 5.8 | 0.3 | 10.1 | 0.3 | 17.5 | 0.9 |
| CC301 | — | — | 2.1 | 0.0 | — | — | — | — | 6.2 | 0.0 | 10.8 | 0.1 |
| CC701 | — | — | 6.8 | 0.1 | — | — | — | — | 18.2 | 0.4 | 28.3 | 0.4 |
| CV201 | — | — | 1.8 | 0.1 | 2.3 | 0.3 | 2.6 | 0.2 | 4.1 | 0.2 | 5.5 | 0.2 |
| CCP201 | — | — | 1.7 | 0.1 | — | — | 2.7 | 0.1 | 4.5 | 0.2 | 7.0 | 0.1 |
| SCP201 | 0.2 | — | 0.4 | — | — | — | 0.6 | — | 1.5 | — | 2.7 | — |

[a]\% represents percentage of released CPT/SN38.
[b]S.D. represents Standard Deviation.

As FIG. 1 and Table 2 show, after 8 hours of dialysis, more than 90% of CPT contained in the CPT-DMSO was dialyzed into the out-of-bag buffer, but only 30% or less percentage of the drugs which were contained in the pharmaceutical compositions were dialyzed into the out-of-bag buffer. FIG. 1 and Table 2 also show that, in general, compared to the polymeric micelles without zwitterions, the polymeric micelles with zwitterions, such as CCP201 and SCP201 compositions, are able to keep drugs encapsulated more effectively.

EXAMPLE 2

Direct Dilution Test

A 150 µL solution of a pharmaceutical composition in accordance with the present disclosure, which was prepared according to the method as set forth above, was mixed with 1350 µL of PBS (pH 7.4), and then incubated at 37° C. After 1, 2, 4, and 8 hours of incubation, 10 µL incubated solutions were taken respectively, and each was mixed with 990 µL of methanol. The quantity of lactone form CPT or SN38 in the mixtures was determined by HPLC. A 150 µL CPT containing DMSO solution (CPT-DMSO) was used as a control.

Figure 2:
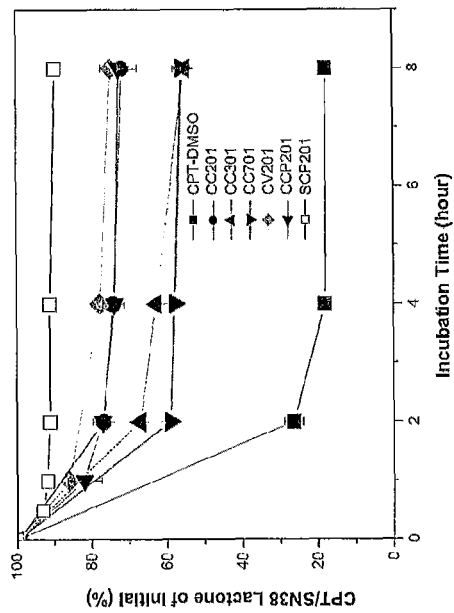
FIG. 2 illustrates the proportion of remained lactone form CPT (or SN38) over incubation time for various compositions using direct dilution method.

FIG. 2 illustrates the proportion of remained lactone form CPT (or SN38) over incubation time for various compositions using direct dilution method and Table 3 shows the original data.

TABLE 3

| | \multicolumn{10}{c}{Hour(s)} |
|---|---|---|---|---|---|---|---|---|---|---|
| | \multicolumn{2}{c}{0.5} | \multicolumn{2}{c}{1} | \multicolumn{2}{c}{2} | \multicolumn{2}{c}{4} | \multicolumn{2}{c}{8} |
| | \%[a] | S.D.[b] | \% | S.D. | \% | S.D. | \% | S.D. | \% | S.D. |
| CPT-DMSO | — | — | — | — | 26.4 | 2.4 | 18.1 | 0.8 | 17.9 | 0.8 |
| CC201 | — | — | — | — | 77.3 | 2.8 | 74.6 | 2.9 | 72.2 | 2.1 |
| CC301 | — | — | — | — | 67.3 | 1.4 | 63.0 | 0.8 | 55.4 | 0.7 |
| CC701 | — | — | — | — | 59.3 | 1.0 | 58.1 | 1.4 | 56.2 | 2.1 |
| CV201 | — | — | 86.0 | 0.6 | — | — | 78.0 | — | 75.0 | 1.8 |
| CCP201 | — | — | 82.4 | 4.5 | 77.5 | 1.1 | 74.3 | 0.9 | 73.0 | 4.9 |
| SCP201 | 93.0 | — | 91.8 | — | 91.1 | — | 91.1 | — | 89.7 | — |

[a]\% represents percentage of remained lactone form CPT and SN38.

[b]S.D. represents Standard Deviation.

As FIG. 2 and Table 3 show, after 8 hours of incubation, only about 20% of CPT in the CPT-DMSO remained in lactone form, but more than 50% of the CPT and SN38, which was originally contained in the pharmaceutical compositions remained in lactone form. FIG. 2 and Table 3 also show that, in general, compared to the polymeric micelles without zwitterions, the polymeric micelles with zwitterions, such as CCP201 and SCP201 compositions, are able to keep CPT and SN38 in lactone form more efficiently.

EXAMPLE 3

In Vivo Kinetic Test of CPT

A 1 mg/kg dose of CPT in DMSO, CC201, CCP201, and CV201 was introduced into SD mice through vein injection, respectively. The concentrations of lactone form CPT in bloods over the time were then determined by HPLC.

Figure 3:
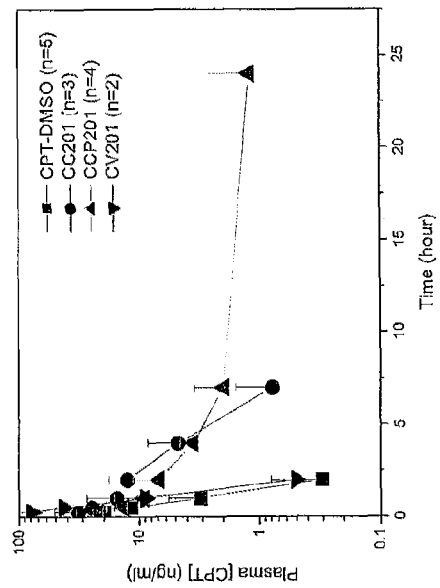
FIG. 3 illustrates the quantitative profile of lactone form CPT in plasma after injection in the in vivo kinetic test.

FIG. 3 illustrates the quantitative profile of lactone form CPT in plasma after injection in the in vivo kinetic test and Table 4 shows the original data.

According to Table 5, after 4 hours, only a trace amount of the lactone form CPT was found in blood while using CPT-DMSO, but in contrast significantly higher plasma lactone form CPT concentrations were found while using 00201, CV201, and CCP201 compositions. Table 5 indicates that CCP201 provided the best protection to lactone form CPT in blood, as the $T_{1/2}$ (hr) and $AUC_{INF}$(hr*ng/ml) values of the plasma lactone form CPT in CCP201 were about 4 and 9.5 times higher than those of the CPT-DMSO, and that, compared to the polymeric micelles without zwitterions, the polymeric micelles with zwitterions, such as CCP201, are able to keep CPT in lactone form in blood more efficiently. Furthermore, Table 5 suggests that this exemplary embodiment of the invention is able to substantially improve the stability of lactone form CPT at the presence of HSA and lower the amount of CPT that would be converted into the carboxylate form at the presence of HSA.

TABLE 4

| | Hour(s) | | | | | | | | | |
|---|---|---|---|---|---|---|---|---|---|---|
| | 0.25 | | 0.5 | | 1 | | 2 | | 4 | |
| | ng/ml | S.D.[a] | ng/ml | S.D. | ng/ml | S.D. | ng/ml | S.D. | ng/ml | S.D. |
| CPT-DMSO | 19.4 | 5.8 | 11.6 | 4.7 | 3.1 | 2.6 | 0.3 | 0.5 | N.D.[b] | N.D. |
| CC201 | 33.3 | 19.1 | 25.6 | 11.4 | 15.8 | 12.9 | 12.9 | 5.6 | 4.9 | 3.9 |
| CCP201 | 22.3 | 12.6 | 13.8 | 5.0 | 9.3 | 7.5 | 6.9 | 4.7 | 3.6 | 1.1 |
| CV201 | 80.0 | 5.7 | 43.0 | 4.2 | 9.0 | 0.3 | 0.5 | 0 | N.D. | N.D. |

| | Hour(s) | | | |
|---|---|---|---|---|
| | 7 | | 24 | |
| | ng/ml | S.D. | ng/ml | S.D. |
| CPT-DMSO | N.D. | N.D. | N.D. | N.D. |
| CC201 | 0.8 | 0.8 | N.D. | N.D. |
| CCP201 | 2.0 | 1.5 | 1.2 | 1.4 |
| CV201 | N.D. | N.D. | N.D. | N.D. |

[a]S.D. represents Standard Deviation.
[b]N.D. represents Not Detectable.
ng represents $10^{-9}$ g.

Table 5 shows the kinetic data. $T_{1/2}$ (hr), $AUC_{INF}$(hr*ng/ml), CL(mL/hr/kg), and Vss (mL/kg) in Table 2 represent half-life time, area under the curve to infinity, clearance, and volume of distribution at steady state, and the units thereof, respectively. The n represents sample number. These parameters can be measured and/or calculated according to the techniques known in the art.

TABLE 5

| | CPT-DMSO | CC201 | CV201 | CCP201 |
|---|---|---|---|---|
| $T_{1/2}$ (hr) | 0.25 ± 0.1 | 1.19 ± 0.32 | 0.24 ± 0.00 | 2.39 ± 1.6 |
| $AUC_{INF}$(hr*ng/ml) | 16 ± 6 | 77 ± 12 | 62 ± 4 | 63 ± 24 |
| CL(mL/hr/kg) | 69403 ± 24178 | 16181 ± 938 | 13127 ± 2001 | 18045 ± 8008 |
| Vss (mL/kg) | 23936 ± 6196 | 21409 ± 7459 | 5689 ± 5146 | 68772 ± 39936 |

EXAMPLE 4

In Vivo Kinetic Test of SN38

A 4 mg/kg dose of SN38 in DMSO, SC201, and SCP201 was introduced into SD mice through vein injection, respectively. The concentrations of lactone form SN38 in bloods over the time were then determined by HPLC.

Figure 4:
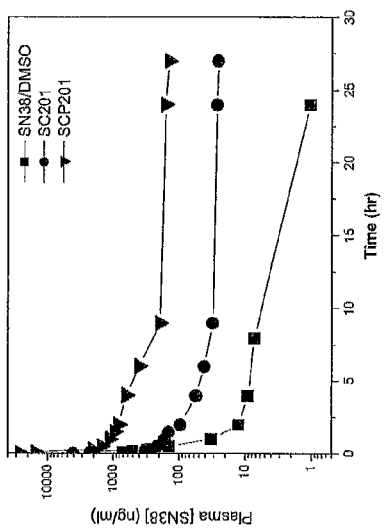
FIG. 4 illustrates the quantitative profile of lactone form SN38 in plasma after injection in the in vivo kinetic test.

FIG. 4 illustrates the quantitative profile of lactone form SN38 in plasma after injection in the in vivo kinetic test and Table 6 shows the original data.

twice a week and five times in total. The tumor size and weight of each mouse was monitored. The tumor size was measured and calculated according to the formula $V=\frac{1}{2} ab^2$, wherein V is the volume of the tumor, a is the longest diameter of the tumor, and b is the shortest diameter of the tumor.

TABLE 6

| | \multicolumn{8}{c}{Hour(s)} | | | | | | | |
|---|---|---|---|---|---|---|---|---|
| | 0.033 ng/ml (S.D.[a]) | 0.083 ng/ml (S.D.) | 0.1 ng/ml (S.D.) | 0.2 ng/ml (S.D.) | 0.250 ng/ml (S.D.) | 0.3 ng/ml (S.D.) | 0.500 ng/ml (S.D.) | 1.0 ng/ml (S.D.) |
| SC201 | 4137.6 (868.9) | 2265.2 (158.6) | — (—) | — (—) | 320.8 (35.3) | — (—) | 213.2 (27.8) | 164.2 (49.3) |
| SCP201 | 26066.6 (2737.0) | 15176.9 (1745.5) | — (—) | — (—) | 2053.0 (277.2) | — (—) | 1503.2 (75.2) | 1127.2 (126.2) |
| SN38-DMSO | — (—) | — (—) | 710.8 (61.7) | 505.3 (109.2) | — (—) | 265.3 (5.6) | 143.4 (27.3) | 32.3 (3.6) |

| | \multicolumn{7}{c}{Day(s)} | | | | | | |
|---|---|---|---|---|---|---|---|
| | 1.5 ng/ml (S.D.) | 2.0 ng/ml (S.D.) | 4.0 ng/ml (S.D.) | 6.0 ng/ml (S.D.) | 8.0 ng/ml (S.D.) | 9.0 ng/ml (S.D.) | 24.0 ng/ml (S.D.) | 27.0 ng/ml (S.D.) |
| SC201 | 144.0 (17.3) | 95.5 (39.2) | 55.6 (0.6) | 41.8 (3.8) | — (—) | 30.9 (8.3) | 26.8 (8.3) | 25.7 (0.3) |
| SCP201 | 936.1 (56.2) | 826.1 (74.4) | 631.0 (66.3) | 398.1 (83.6) | — (—) | 194.7 (9.8) | 160.5 (17.7) | 141.3 (11.3) |
| SN38-DMSO | — (—) | 12.5 (0.5) | 9.0 (0.6) | — (—) | 7.3 (0.7) | — (—) | 1.0 (0.30) | — (—) |

[a]S.D. represents Standard Deviation.

Table 7 shows the kinetic data. $T_{1/2}$ (hr), $AUC_{INF}$(hr*ng/ml), CL(mL/hr/kg), and Vss (mL/kg) in Table 7 represent half-life time, maximum concentration, area under the curve to infinity, clearance, and volume of distribution at steady state, and the units thereof, respectively. The n represents sample number. These parameters can be measured and/or calculated according to the techniques known in the art.

TABLE 7

| | SN38-DMSO | SC201 | SCP201 |
|---|---|---|---|
| $T_{1/2}$ (hr) | 6.2 | 14.8 | 12.7 |
| $AUC_{INF}$(hr*ng/ml) | 417 | 2370 | 20030 |
| CL(mL/hr/kg) | 2490 | 834 | 960 |
| Vss (mL/kg) | 34300 | 34900 | 62300 |

According to Table 7, after 4 hours, only limited amount of SN38 was found in blood while using SN38-DMSO, but in contrast significantly higher plasma SN38 were found while using SC201 and SCP201. Table 7 indicates that SCP201 provided the best protection to SN38 in blood, as the $T_{1/2}$ (hr) and $AUC_{INF}$(hr*ng/ml) values of the plasma SN38 in SCP201 were about 2 and 50 times higher than those of the SN38-DMSO respectively.

EXAMPLE 5

In Vivo Pharmaceutical Efficiency Comparison of CCP201 with Free CPT11

Figure 5:
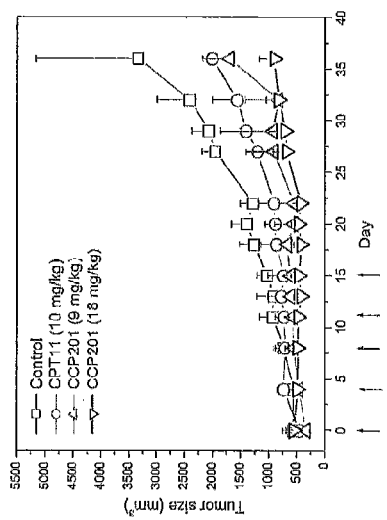
FIG. 5 illustrates the size of HT29 tumor after CCP201 and free CPT11 treatments.

Human colon cancer HT29 cells were implanted subcutaneously at the dorsal muscles of immunodeficiency mice. After the tumor size reached about 300-500 mm³, the mice were randomly divided into 4 groups, and then saline, CPT11, and CCP201 were introduced into the mice through vein injection, respectively. The administration frequency was FIG. 5 illustrates the size of HT29 tumor after CCP201 and free CPT11 treatments. Table 8 shows the original data and Table 9 shows the summarized data. The results suggest that, in general, CCP201 is able to provide higher pharmaceutical efficiency or potency than free CPT11. In particular, the tumor inhibition rate of the 18 mg/kg CCP201 dose was more than 60%, which was significantly higher than that of free CPT11.

TABLE 8

| | \multicolumn{5}{c}{Day(s)} | | | | |
|---|---|---|---|---|---|
| | 0 | 4 | 8 | 11 | 13 |
| | \multicolumn{5}{c}{Tumor Size (mm³)} | | | | |
| | Vol. (S.D.[a]) | Vol. (S.D.) | Vol. (S.D.) | Vol. (S.D.) | Vol. (S.D.) |
| CONTROL | 561.4 (132.8) | 548.9 (83.5) | 730.3 (144.8) | 927.0 (235.7) | 914.1 (301.6) |
| CPT11 (10 mg/kg) | 469.6 (136.6) | 745.8 (119.5) | 723.4 (199.3) | 740.8 (154.5) | 786.0 (251.4) |
| CCP201 (9 mg/kg) | 337.0 (84.1) | 469.9 (91.2) | 556.5 (100.7) | 575.8 (79.9) | 614.3 (88.6) |
| CCP201 (18 mg/kg) | 557.5 (204.7) | 492.2 (141.9) | 487.1 (224.5) | 479.3 (167.6) | 427.8 (131.9) |

| | \multicolumn{5}{c}{Day(s)} | | | | |
|---|---|---|---|---|---|
| | 15 | 18 | 20 | 22 | 27 |
| | \multicolumn{5}{c}{Tumor Size (mm³)} | | | | |
| | Vol. (S.D.) | Vol. (S.D.) | Vol. (S.D.) | Vol. (S.D.) | Vol. (S.D.) |
| CONTROL | 1024.4 (190.4) | 1259.8 (267.2) | 1391.6 (275.5) | 1284.0 (227.6) | 1958.5 (236.8) |
| CPT11 (10 mg/kg) | 757.5 (280.9) | 879.8 (275.0) | 902.7 (179.2) | 927.3 (270.8) | 1217.6 (209.4) |
| CCP201 (9 mg/kg) | 621.2 (62.3) | 675.0 (118.8) | 565.2 (334.8) | 554.7 (290.4) | 924.0 (370.2) |

TABLE 8-continued

| | | | | | |
|---|---|---|---|---|---|
| CCP201 (18 mg/kg) | 468.7 (140.8) | 427.8 (131.9) | 473.3 (132.8) | 436.7 (68.2) | 685.2 (245.7) |

[a]S.D. represents Standard Deviation.

TABLE 9

| Group | Dose (mg/kg) | Total dose (mg/kg) | TIR %[a] (day 21) | Maximum weight loss % (day)[b] |
|---|---|---|---|---|
| CONTROL | — | — | — | 14.8 (13) |
| CPT11 | 10 | 50 | 35 | 17.3 (27) |
| CCP201 | 9 | 45 | 59 | 20.0 (15) |
| CCP201 | 18 | 90 | 66 | 32.6 (15) |

[a]TIR (%): tumor inhibition rate = $(1 - V_{treatment}/V_{control})*100$
[b]Maximum body weight was measured after first treatment.

EXAMPLE 6

In Vivo Pharmaceutical Efficiency Comparison of SN38 with Free CPT 11

Human colon cancer HT29 cells were implanted subcutaneously at the dorsal muscles of immunodeficiency mice. After the tumor size reached about 100-200 mm³, the mice were randomly divided into 5 groups, and then saline, CPT11, and SCP201 were introduced into the mice through vein injection, respectively. The administration frequency was twice a week and five times in total. The tumor size and weight of each mouse was monitored. The tumor size was measured and calculated according to the formula V=1/2 ab², wherein V is the volume of tumor, a is the longest diameter of the tumor, and b is the shortest diameter of the tumor. Human colon cancer Colo205 cells were also tested by the same method described above, except that the mice were divided into 6 groups.

Figure 6:
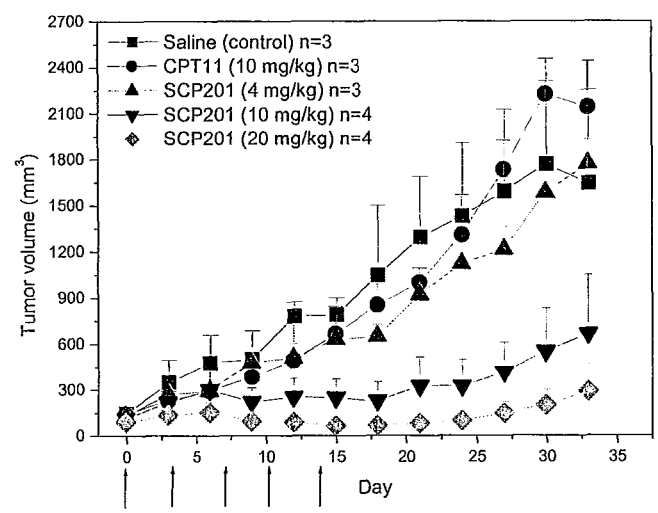
FIG. 6 illustrates the size of HT29 tumor after SCP201 and free CPT11 treatments.

FIG. 6 illustrates the size of HT29 tumor after SCP201 and free CPT11 treatments. Table 10 shows the original data and Table 11 shows the summarized data.

TABLE 10

| | Day(s) | | | | |
|---|---|---|---|---|---|
| | 0 | 3 | 6 | 9 | 12 |
| | Tumor Size (mm³) | | | | |
| | Vol. (S.D.[a]) | Vol. (S.D.) | Vol. (S.D.) | Vol. (S.D.) | Vol. (S.D.) |
| CONTROL | 144.3 (44.1) | 346.5 (146.8) | 476.7 (182.5) | 499.3 (187.9) | 781.3 (91.1) |
| CPT11 (10 mg/kg) | 142.8 (47.6) | 227.8 (62.7) | 292.7 (119.7) | 384.2 (158.4) | 492.0 (241.5) |
| SCP201 (4 mg/kg) | 130.5 (40.8) | 270.7 (87.3) | 295 (38.1) | 480.3 (51.4) | 511.3 (94.3) |
| SCP201 (10 mg/kg) | 114.6 (31.1) | 218.8 (78.3) | 300.5 (136.1) | 221.8 (92.8) | 254.1 (120.4) |
| SCP201 (20 mg/kg) | 90.5 (27.7) | 137.4 (48.4) | 155.3 (64.3) | 97.4 (40.0) | 90.5 (36.4) |

| | Day(s) | | | | |
|---|---|---|---|---|---|
| | 15 | 18 | 21 | 24 | 27 |
| | Tumor Size (mm³) | | | | |
| | Vol. (S.D.) | Vol. (S.D.) | Vol. (S.D.) | Vol. (S.D.) | Vol. (S.D.) |
| CONTROL | 789.3 (109.4) | 1045.8 (454.1) | 1293.2 (393.5) | 1429.8 (475.3) | 1590.7 (534.6) |
| CPT11 (10 mg/kg) | 666.0 (177.3) | 853.5 (170.4) | 997.7 (93.5) | 1308.5 (256.5) | 1732.2 (189.7) |
| SCP201 (4 mg/kg) | 634.2 (71.2) | 650.8 (76.7) | 922 (117.0) | 1122.7 (173.5) | 1216 (145.7) |
| SCP201 (10 mg/kg) | 249.6 (122.0) | 227.8 (122.0) | 324.9 (190.1) | 323.6 (174.6) | 416.1 (194.3) |
| SCP201 (20 mg/kg) | 67.0 (22.5) | 70.1 (22.5) | 82.9 (27.9) | 100.4 (42.3) | 149.0 (71.0) |

[a]S.D. represents Standard Deviation.

TABLE 11

| Group | Dose (mg/kg) | Total dose (mg/kg) | TIR %[a] (day 21) | Maximum weight loss % (day)[b] |
|---|---|---|---|---|
| CONTROL | — | — | — | 5.3 (21) |
| CPT11 | 10 | 50 | 23 | 9.4 (27) |
| SCP201 | 4 | 20 | 29 | 11.8 (18) |
| SCP201 | 10 | 50 | 75 | 8.8 (15) |
| SCP201 | 20 | 100 | 94 | 15.0 (12) |

Figure 7:
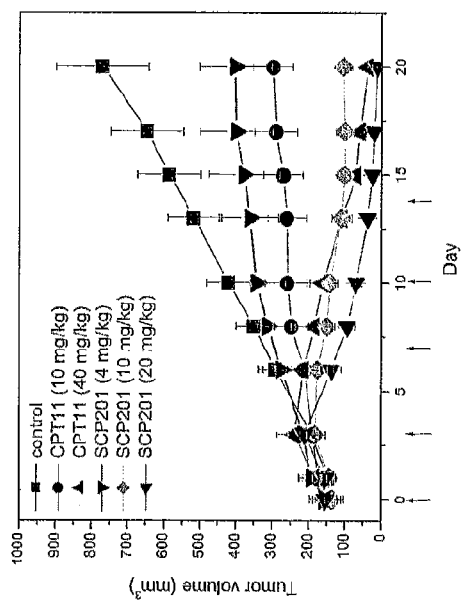
FIG. 7 illustrates the size of Colo205 tumor after SCP201 and free CPT11 treatments.

[a]TIR (%) and: tumor inhibition rate = $(1 - V_{treatment}/V_{control})*100$
[b]Maximum body weight was measured after first treatment FIG. 7 illustrates the size of Colo205 tumor after SCP201 and free CPT11 treatments. Table 12 shows the original data and Table 13 shows summarized data.

TABLE 12

| | Day(s) | | | | |
|---|---|---|---|---|---|
| | 0 | 1 | 3 | 6 | 8 |
| | Tumor Size (mm³) | | | | |
| | Vol. (S.D.[a]) | Vol. (S.D.) | Vol. (S.D.) | Vol. (S.D.) | Vol. (S.D.) |
| CONTROL | 150.6 (47.1) | 147.5 (22.5) | 191.5 (35.5) | 292.7 (46.5) | 351.9 (48.6) |
| CPT11 (10 mg/kg) | 142.0 (30.1) | 175.1 (34.4) | 192.0 (35.6) | 215.0 (47.5) | 251.2 (47.0) |
| CT11 (40 mg/kg) | 152.1 (27.6) | 184.6 (32.1) | 239.3 (48.5) | 215.0 (51.9) | 184.7 (56.1) |
| SCP201 (4 mg/kg) | 156.1 (33.9) | 192.6 (34.8) | 215.5 (31.6) | 276.9 (50.3) | 313.8 (60.5) |
| SCP201 (10 mg/kg) | 134.1 (23.6) | 142.9 (23.6) | 181.6 (27.7) | 176.1 (23.9) | 151.0 (23.4) |
| SCP201 (20 mg/kg) | 156.7 (33.7) | 157.8 (30.2) | 214.4 (42.9) | 141.1 (29.3) | 97.1 (21.8) |

| | Day(s) | | | | |
|---|---|---|---|---|---|
| | 10 | 13 | 15 | 17 | 20 |
| | Tumor Size (mm³) | | | | |
| | Vol. (S.D.) | Vol. (S.D.) | Vol. (S.D.) | Vol. (S.D.) | Vol. (S.D.) |
| CONTROL | 421.6 (60.4) | 518.3 (71.2) | 587.1 (87.7) | 648.4 (100.0) | 771.8 (128.3) |
| CPT11 (10 mg/kg) | 262.1 (61.1) | 263.5 (53.1) | 274.1 (53.8) | 293.7 (58.9) | 301.4 (55.2) |
| CPT11 (40 mg/kg) | 161.7 (44.5) | 110.2 (28.12) | 70.9 (17.6) | 59.1 (15.9) | 37.8 (8.4) |
| SCP201 (4 mg/kg) | 345.3 (77.3) | 363.6 (79.2) | 380.0 (96.0) | 402.3 (99.7) | 404.6 (99.0) |
| SCP201 (10 mg/kg) | 141.8 (22.5) | 110.7 (21.4) | 101.13 (22.0) | 101.0 (24.5) | 104.8 (25.0) |
| SCP201 (20 mg/kg) | 72.9 (15.3) | 40.7 (8.1) | 27.1 (5.5) | 22.4 (4.4) | 14.4 (4.8) |

[a]S.D. represents Standard Deviation.

TABLE 13

| Group | Dose (mg/kg) | Total dose (mg/kg) | TIR %[a] (day 20) | Maximum weight loss % (day)[b] |
|---|---|---|---|---|
| Control | — | — | — | 3.0 (18) |
| CPT11 | 10 | 50 | 61 | 4.2 (18) |
| CPT11 | 40 | 200 | 95 | 3.7 (8) |
| SCP201 | 4 | 20 | 48 | 3.2 (3) |
| SCP201 | 10 | 50 | 86 | 8.8 (6) |
| SCP201 | 20 | 100 | 98 | 16.1 (15) |

[a]TIR (%): tumor inhibition rate = $(1 - V_{treatment}/V_{control})*100$
[b]Maximum body weight was measured after first treatment FIG. 7, Table 12, and Table 13 show that, in general, SCP201 is able to provide higher pharmaceutical efficiency than free CPT11. In particular, both Table 11 and 13 show that the tumor inhibition rates to HT29 and Colo205 could be higher than 90% while using 20 mg/kg of SCP201.

EXAMPLE 7

In Vitro Pharmaceutical Efficiency Test of SCP201 Using MTT Assay

Various human cancer lines, such as A549, AS2, and H460, were implanted onto multi-well plates and Dulbecco's Modified Eagle Media (high glucose) with 10% of fetal bovine serum and 1% of P/S being added to each well. After 24 hours of $CO_2$ incubation at 37° C., various amounts of CPT11, SN38, and SCP201 were added to each well respectively, and the mixtures were incubated in $CO_2$ for another 72 hours at 37° C. Then a 20 μL of 0.5 mg/ml MTT (3-(4,5-dimethylthiazol-2-yl)-2,5-diphenyltetrazolium bromide) solution was added to each well to start the reaction. After 2 hours, the suspension of each well was removed and DMSO was added into the well to dissolve formazan, which was formed during the reaction. The living cell concentration was then obtained by analyzing the OD570 and OD600 data of each well.

Table 14 shows the selection of cancer cell lines and the half maximum inhibitory concentrations ($IC_{50}$) of CPT11, SN38, and SCP201 to each tumor cell line respectively. The difference of the pharmaceutical activities of CPT11 and SN38 is consistent with data disclosed in publications. Table 14 indicates that the in vitro pharmaceutical activity of the pharmaceutical composition comprising SN38 as disclosed herein was not reduced.

In the present application, the human lung cancer cell line (A549 and AS2) used are provided by Prof. Wu-Chou Su (National Cheng Kung University Hospital College of Medicine, Taiwan). The human colorectal cancer cell line (Colo 205 and HT29) is provided by Dr. Ming-Jium Shieh (National Taiwan University College of Medicine and College of Engineering, Taiwan). The liver cancer cell line SK-HEP-1 is obtained from American Type Culture Collection (ATCC, Rockville, Md.). The rest of cell lines in the application is obtained from Bioresource Collection and Research Center (BCRC, Food Industry Research and Development Institute, Hsinchu, Taiwan).

Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A pharmaceutical composition for treating a tumor, comprising
a polymeric micelle comprising a block copolymer of the following formula:

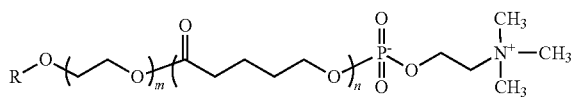

wherein R represents a hydrogen atom, a $C_{1-6}$ alkyl group, a benzyl group or an acyl group; and m and n, which may be the same or different, are each an integer of 10-100) and an anti-tumor drug encapsulated within said polymeric micelle, wherein the anti-tumor drug is 7-ethyl-10-hydroxycamptothecin.

2. The pharmaceutical composition of claim 1, wherein said polymeric micelle has a diameter ranging from about 20 nm to about 1,000 nm.

3. The pharmaceutical composition of claim 1, wherein said polymeric micelle has a hydrophobic interior and a hydrophilic surface.

4. The pharmaceutical composition of claim 1, wherein said composition is suitable for treating a solid tumor.

TABLE 14

| | | $IC_{50}$ | | |
|---|---|---|---|---|
| Indication | Cell-line | CPT11 (mg/ml) | SN38 (ng/ml) | SCP201 (ng/ml) |
| Lung | A549 | 13.34 ± 1.33 | 13.87 ± 1.23 | 11.96 ± 0.94 |
| | AS2 | 4.20 ± 0.48 | 1.76 ± 0.23 | 2.79 ± 0.53 |
| | H460 | 1.89 ± 0.14 | 3.18 ± 0.26 | 8.72 ± 0.30 |
| Colorectal | HT29 | 1.90 | 3.40 | 5.80 |
| | Colo 205 | 6.84 ± 0.99 | 5.63 ± 0.96 | 5.72 ± 0.60 |
| Liver | hepG2/C3A | N.D.[a] | 28.70 ± 9.20 | 9.97 ± 2.67 |
| | SK-HEP-1 | N.D. | 15.21 ± 1.33 | 25.67 ± 1.40 |
| Stomach | AGS | N.D. | 40.22 ± 14.24 | 36.42 ± 12.95 |
| Prostate | PC-3 | N.D. | 95.9 ± 21.27 | 105.48 ± 34.23 |
| Brain | U-87 MG | N.D. | 10.22 ± 2.60 | 9.99 ± 3.00 |
| Breast | MCF-7 | N.D. | 60.93 ± 48.86 | 89.33 ± 69.47 |
| Ovarian | OVCAR-3 | 16.75 ± 1.43 | 22.73 ± 2.14 | 28.10 ± 1.69 |
| Bladder | 5637 | 1.42 ± 0.10 | 0.36 ± 0.03 | 0.64 ± 0.07 |
| Nasalseptum | RPMI2650 | 1.47 ± 0.26 | 0.97 ± 0.07 | 1.22 ± 0.11 |
| Tongue | SCC-25 | 12.35 ± 1.16 | 19.71 ± 11.28 | 27.06 ± 23.48 |

[a]N.D represent Not do.

5. The pharmaceutical composition of claim 1, wherein said block copolymer is biodegradable.

6. The pharmaceutical composition of claim 1, wherein said block copolymer is biocompatible.

7. A method of enhancing the water-solubility of an anti-tumor drug, comprising:

forming a polymeric micelle, comprising a block copolymer of the following formula:

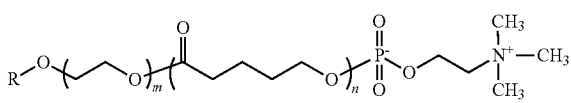

wherein R represents a hydrogen atom, a $C_{1-6}$ alkyl group, a benzyl group or an acyl group; and m and n, which may be the same or different, are each an integer of 10-100; and encapsulating the anti-tumor drug within said polymeric micelle, wherein the anti-tumor drug is 7-ethyl-10-hydroxycamptothecin.

8. A method of increasing the blood circulating time of an anti-tumor drug, comprising:

forming a polymeric micelle, comprising a block copolymer of the following formula:

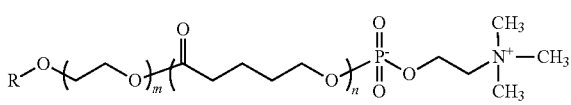

wherein R represents a hydrogen atom, a $C_{1-6}$ alkyl group, a benzyl group or an acyl group; and m and n, which may be the same or different, are each an integer of 10-100; and encapsulating the anti-tumor drug within said polymeric micelle, wherein the anti-tumor drug is 7-ethyl-10-hydroxycamptothecin; and administering the encapsulated anti-tumor drug to a subject.

9. A method of delivering an anti-tumor drug to a solid tumor, comprising:

forming a polymeric micelle, comprising a block copolymer of the following formula:

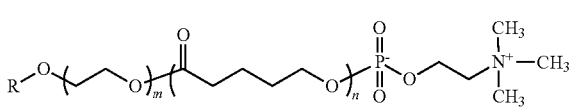

wherein R represents a hydrogen atom, a $C_{1-6}$ alkyl group, a benzyl group or an acyl group; and m and n, which may be the same or different, are each an integer of 10-100;

encapsulating the anti-tumor drug within said polymeric micelle, wherein the anti-tumor drug is 7-ethyl-10-hydroxycamptothecin to form an encapsulation complex; and introducing the encapsulation complex into a human body.

\* \* \* \* \*